United States Patent
Gautam et al.

(10) Patent No.: US 9,498,317 B2
(45) Date of Patent: Nov. 22, 2016

(54) PROSTHETIC HEART VALVE DELIVERY SYSTEMS AND PACKAGING

(75) Inventors: Abhishek Gautam, Upper West Herkimer, NY (US); Gregory A. Wright, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 204 days.

(21) Appl. No.: 13/324,124

(22) Filed: Dec. 13, 2011

(65) Prior Publication Data

US 2012/0158128 A1    Jun. 21, 2012

Related U.S. Application Data

(60) Provisional application No. 61/423,785, filed on Dec. 16, 2010.

(51) Int. Cl.
*A61F 2/24* (2006.01)
*A61F 2/00* (2006.01)

(52) U.S. Cl.
CPC ............ *A61F 2/0095* (2013.01); *A61F 2/2412* (2013.01); *A61F 2/2427* (2013.01)

(58) Field of Classification Search
CPC . A61B 19/026; A61B 19/206; A61F 2/0095; A61F 2/2412; A61F 2/2427
USPC .................. 623/2.1, 2.11; 206/438
See application file for complete search history.

(56) References Cited

U.S. PATENT DOCUMENTS

| | | | |
|---|---|---|---|
| 3,394,954 A * | 7/1968 | Sarns | 285/319 |
| 3,818,894 A | 6/1974 | Wichterle et al. | |
| 4,011,947 A * | 3/1977 | Sawyer | 206/363 |
| 4,101,031 A | 7/1978 | Cromie | |
| 4,182,446 A | 1/1980 | Penny | |
| 4,206,844 A | 6/1980 | Thukamoto et al. | |
| 4,211,325 A | 7/1980 | Wright | |
| 4,329,076 A * | 5/1982 | Coreth | 403/109.8 |

(Continued)

FOREIGN PATENT DOCUMENTS

| | | |
|---|---|---|
| DE | 102006027304 A1 | 12/2007 |
| EP | 0169259 A1 | 1/1986 |

(Continued)

OTHER PUBLICATIONS

International Search Report from corresponding International Application No. PCT.US2011/065073 dated Dec. 15, 2011.

*Primary Examiner* — Richard Louis
(74) *Attorney, Agent, or Firm* — Michelle C. Kim; AnneMarie Kaiser; Pui Tong Ho

(57) ABSTRACT

Packaging for dry prosthetic tissue heart valves and their delivery systems includes a primary sterile barrier that permits gas sterilization of the tissue implant, and a secondary sterile barrier that also prevents oxidation of the implant during long-term storage. Dry tissue heart valves and their delivery systems are placed within a primary container such as a rigid tray that limits movement of the components therein. The primary container is placed within a secondary container, and the assembly is then sterilized. The outer sterile barrier may include a double seal so that a first gas-permeable seal can be closed for sterilization, after which a second gas-impermeable seal can be closed to seal out any further oxygen contact with the tissue implant. A collapsible delivery handle for a surgical heart valve may be provided which reduces the size of the packaging.

19 Claims, 10 Drawing Sheets

(56) References Cited

U.S. PATENT DOCUMENTS

| | | | |
|---|---|---|---|
| 4,357,274 A | 11/1982 | Werner | |
| 4,657,133 A * | 4/1987 | Komatsu et al. | 206/204 |
| 4,697,703 A | 10/1987 | Will | |
| 4,743,231 A * | 5/1988 | Kay et al. | 604/180 |
| 4,801,015 A | 1/1989 | Lubock et al. | |
| 4,865,871 A | 9/1989 | Livesey et al. | |
| 4,891,319 A | 1/1990 | Roser | |
| 5,167,223 A | 12/1992 | Koros et al. | |
| 5,200,399 A | 4/1993 | Wettlaufer et al. | |
| 5,236,450 A | 8/1993 | Scott | |
| 5,292,802 A | 3/1994 | Rhee et al. | |
| 5,298,254 A | 3/1994 | Prewett et al. | |
| 5,306,500 A | 4/1994 | Rhee et al. | |
| 5,336,616 A | 8/1994 | Livesey et al. | |
| 5,476,516 A | 12/1995 | Seifter et al. | |
| 5,480,425 A | 1/1996 | Ogilive | |
| 5,531,785 A | 7/1996 | Love et al. | |
| 5,560,487 A | 10/1996 | Starr | |
| 5,578,076 A | 11/1996 | Krueger et al. | |
| 5,582,607 A | 12/1996 | Lackman | |
| 5,591,194 A * | 1/1997 | Berthiaume | 606/192 |
| 5,615,770 A | 4/1997 | Applebaum et al. | |
| 5,690,226 A | 11/1997 | N'Guyen | |
| 5,720,391 A | 2/1998 | Dohm et al. | |
| 5,776,187 A | 7/1998 | Krueger et al. | |
| 5,782,914 A | 7/1998 | Schankereli | |
| 5,800,531 A | 9/1998 | Cosgrove et al. | |
| 5,810,876 A * | 9/1998 | Kelleher | 606/205 |
| 5,823,342 A | 10/1998 | Caudillo et al. | |
| 5,856,102 A | 1/1999 | Bierke-Nelson et al. | |
| 5,868,253 A | 2/1999 | Krueger et al. | |
| 5,972,014 A * | 10/1999 | Nevins | 606/185 |
| 5,980,569 A | 11/1999 | Scirica | |
| 5,984,959 A | 11/1999 | Robertson et al. | |
| 6,126,007 A | 10/2000 | Kari et al. | |
| 6,197,053 B1 | 3/2001 | Cosgrove et al. | |
| 6,199,696 B1 | 3/2001 | Lytle et al. | |
| 6,293,970 B1 | 9/2001 | Wolfinbarger, Jr. et al. | |
| 6,312,474 B1 | 11/2001 | Francis et al. | |
| 6,416,547 B1 | 7/2002 | Erickson et al. | |
| 6,534,004 B2 * | 3/2003 | Chen et al. | 422/40 |
| 6,544,289 B2 | 4/2003 | Wolfinbarger, Jr. et al. | |
| 6,569,200 B2 | 5/2003 | Wolfinbarger, Jr. et al. | |
| 6,589,591 B1 | 7/2003 | Mansouri et al. | |
| 6,591,998 B2 | 7/2003 | Haynes et al. | |
| 6,622,864 B1 | 9/2003 | Debbs et al. | |
| 6,652,594 B2 | 11/2003 | Francis et al. | |
| 6,736,845 B2 | 5/2004 | Marquez et al. | |
| 6,919,172 B2 | 7/2005 | DePablo et al. | |
| 6,962,774 B2 | 11/2005 | Okuda et al. | |
| 6,966,925 B2 | 11/2005 | Stobie | |
| 7,063,726 B2 | 6/2006 | Crouch et al. | |
| 7,176,256 B2 | 2/2007 | Rhee et al. | |
| 7,389,874 B2 | 6/2008 | Quest et al. | |
| 7,699,168 B2 | 4/2010 | Ryan et al. | |
| 7,712,606 B2 | 5/2010 | Salahieh et al. | |
| 7,806,926 B2 | 10/2010 | Stobie | |
| 7,842,084 B2 | 11/2010 | Bicer | |
| 7,866,468 B2 * | 1/2011 | Kyritsis | 206/363 |
| 8,105,375 B2 | 1/2012 | Navia et al. | |
| 8,187,324 B2 | 5/2012 | Webler et al. | |
| 8,361,144 B2 | 1/2013 | Fish et al. | |
| 2001/0023372 A1 | 9/2001 | Chen et al. | |
| 2002/0013621 A1 * | 1/2002 | Stobie et al. | 623/2.11 |
| 2002/0138137 A1 * | 9/2002 | Cox | 623/2.13 |
| 2003/0083752 A1 | 5/2003 | Wolfinbarger et al. | |
| 2003/0125805 A1 * | 7/2003 | Johnson et al. | 623/2.11 |
| 2003/0203183 A1 * | 10/2003 | Hester et al. | 428/315.5 |
| 2003/0217415 A1 | 11/2003 | Crouch et al. | |
| 2004/0093004 A1 * | 5/2004 | Schultz | 606/192 |
| 2004/0148017 A1 | 7/2004 | Stobie | |
| 2004/0176798 A1 * | 9/2004 | Epstein et al. | 606/213 |
| 2005/0027236 A1 | 2/2005 | Douk | |
| 2005/0113910 A1 | 5/2005 | Paniagua et al. | |
| 2005/0241981 A1 * | 11/2005 | Gupta et al. | 206/524.8 |
| 2005/0246035 A1 | 11/2005 | Wolfinbarger et al. | |
| 2005/0268573 A1 * | 12/2005 | Yan | 53/425 |
| 2006/0073592 A1 | 4/2006 | Sun et al. | |
| 2006/0195183 A1 * | 8/2006 | Navia et al. | 623/2.18 |
| 2007/0061008 A1 * | 3/2007 | Salahieh et al. | 623/2.11 |
| 2007/0104395 A1 * | 5/2007 | Kinigakis et al. | 383/61.1 |
| 2007/0203575 A1 * | 8/2007 | Forster et al. | 623/2.11 |
| 2007/0244551 A1 * | 10/2007 | Stobie | 623/2.1 |
| 2007/0255390 A1 | 11/2007 | Ducke et al. | |
| 2007/0260301 A1 * | 11/2007 | Chuter et al. | 623/1.11 |
| 2008/0033545 A1 * | 2/2008 | Bergin | 623/2.11 |
| 2008/0071367 A1 * | 3/2008 | Bergin et al. | 623/2.11 |
| 2008/0082163 A1 * | 4/2008 | Woo | 623/2.1 |
| 2008/0102439 A1 * | 5/2008 | Tian et al. | 435/1.1 |
| 2008/0183181 A1 * | 7/2008 | Treacy et al. | 606/108 |
| 2009/0130162 A2 | 5/2009 | Pathak et al. | |
| 2009/0182405 A1 * | 7/2009 | Arnault De La Menardiere et al. | 623/1.11 |
| 2009/0236253 A1 * | 9/2009 | Merckle et al. | 206/439 |
| 2009/0292262 A1 * | 11/2009 | Adams et al. | 604/264 |
| 2010/0174363 A1 | 7/2010 | Castro | |
| 2011/0240511 A1 * | 10/2011 | Bolton et al. | 206/532 |
| 2012/0271281 A1 * | 10/2012 | Schertiger | 604/544 |

FOREIGN PATENT DOCUMENTS

| | | |
|---|---|---|
| JP | 2009528089 A | 8/2009 |
| WO | 9510314 A1 | 4/1995 |
| WO | 9640345 A1 | 12/1996 |
| WO | 9807452 A1 | 2/1998 |
| WO | 03006179 A1 | 1/2003 |
| WO | 2005073091 A2 | 8/2005 |
| WO | 2010068527 A1 | 6/2010 |
| WO | 2011109630 A2 | 9/2011 |

* cited by examiner

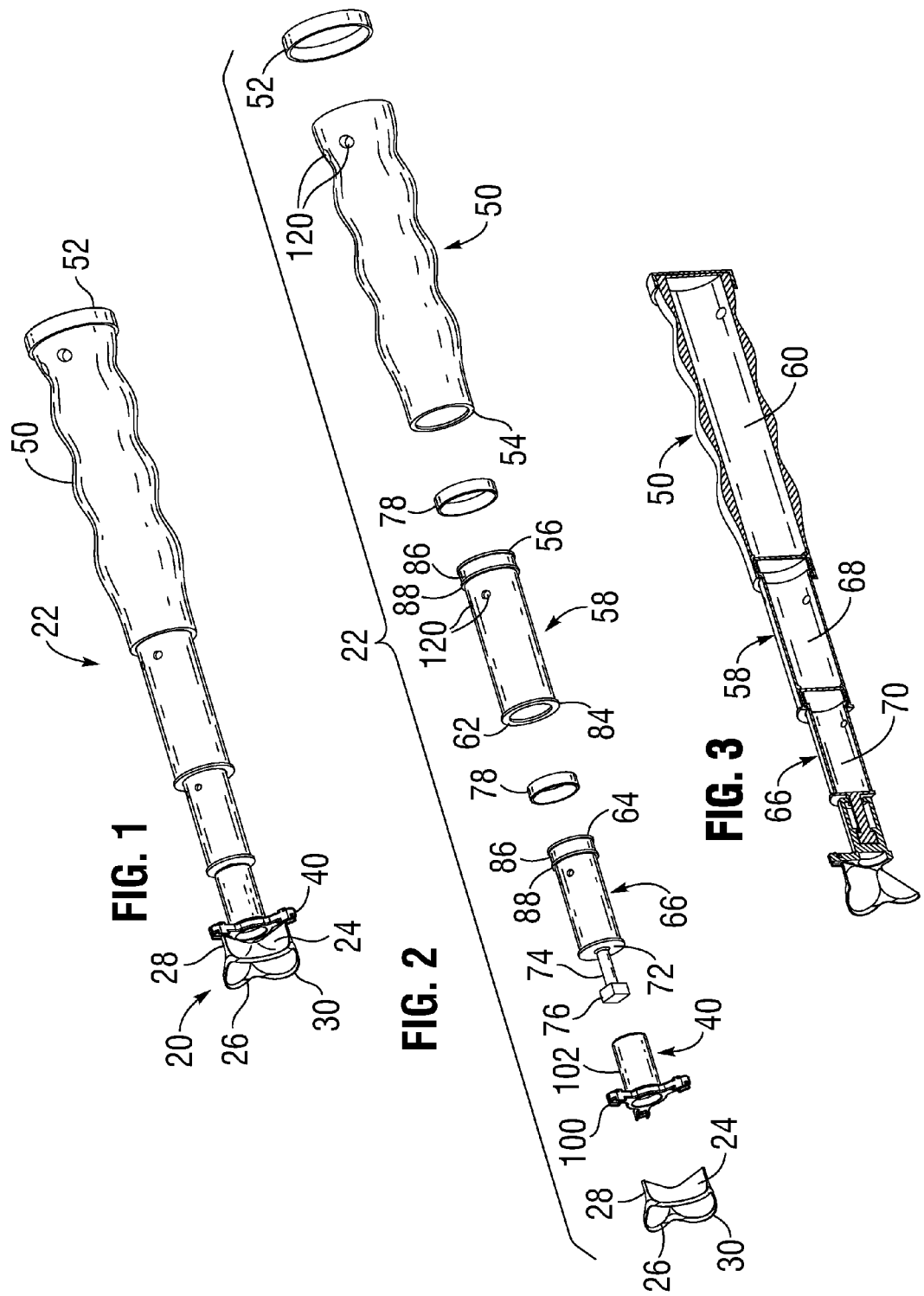

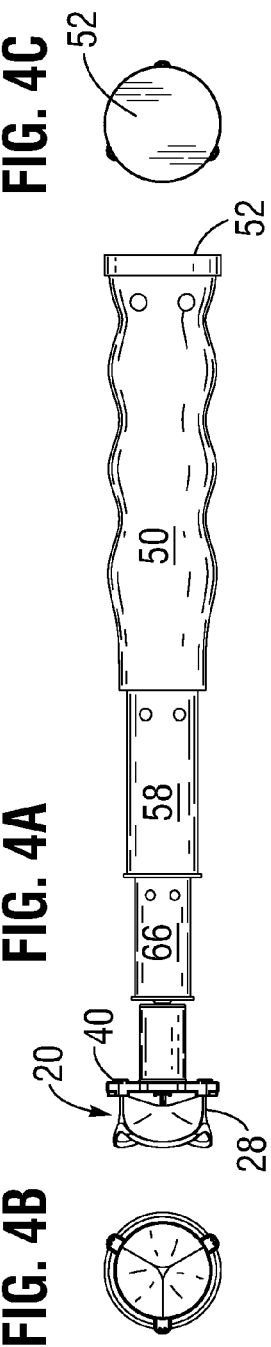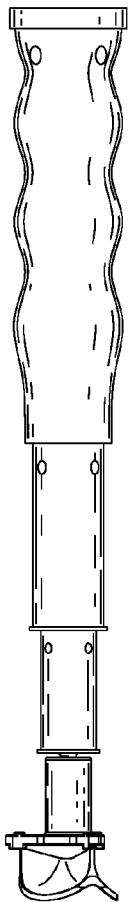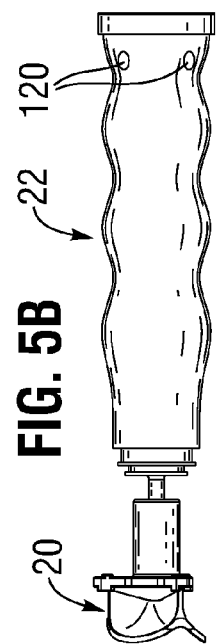

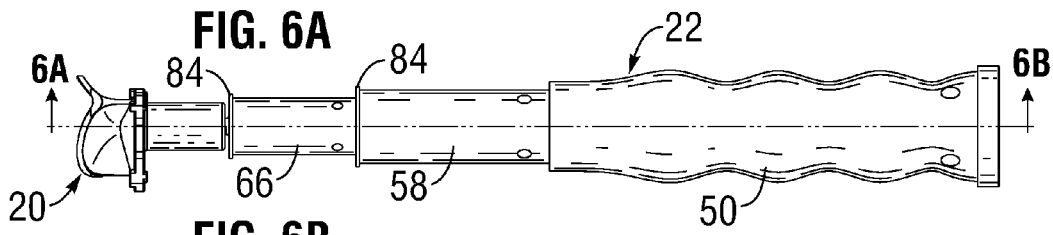
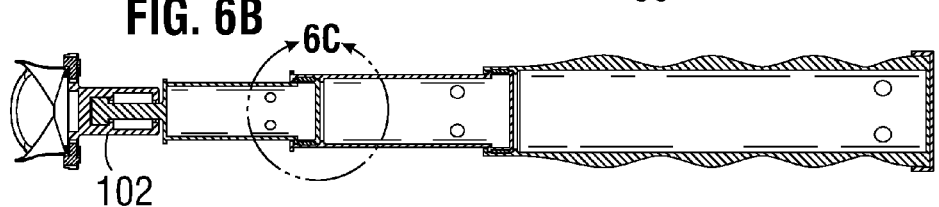
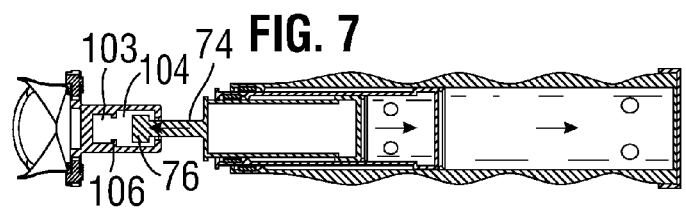
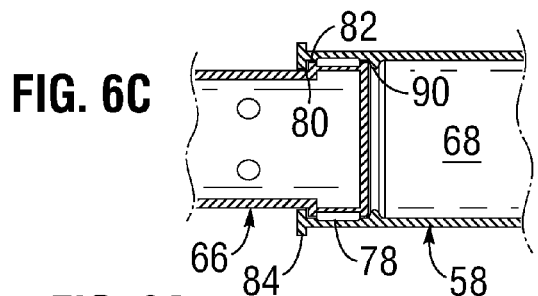
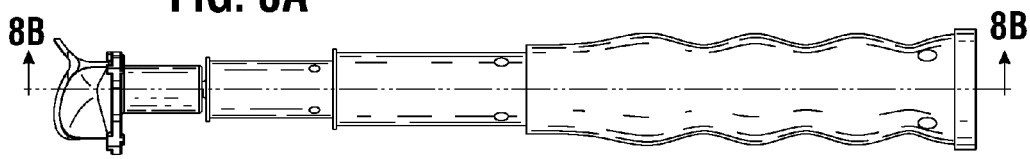
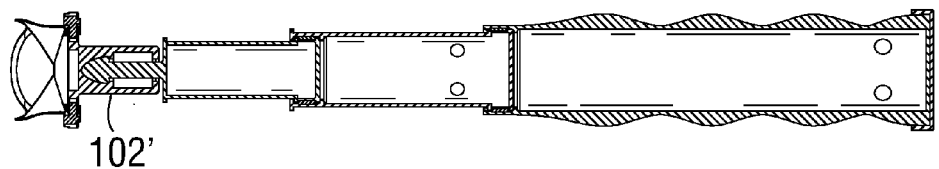
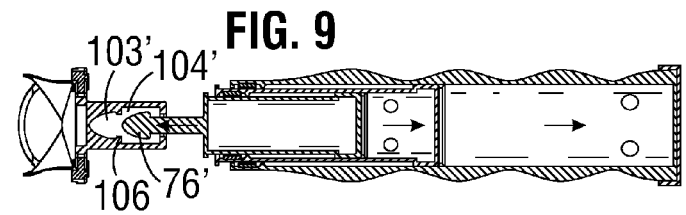

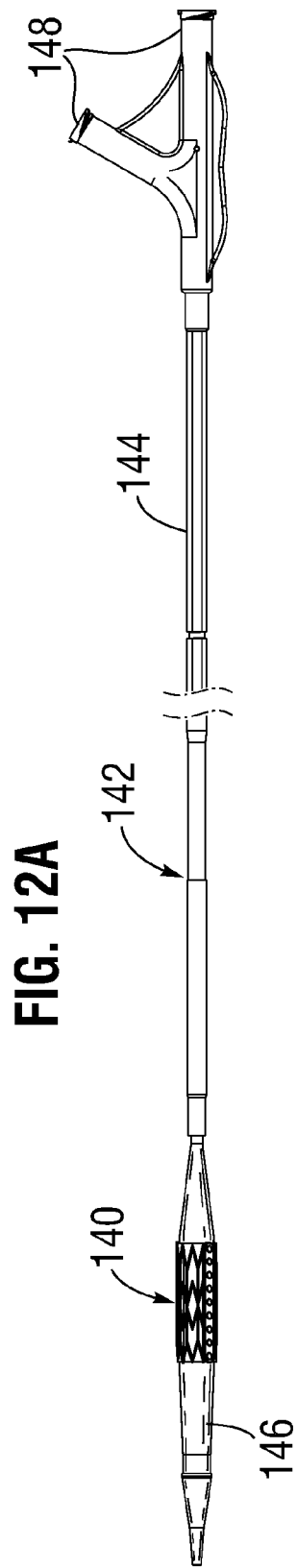
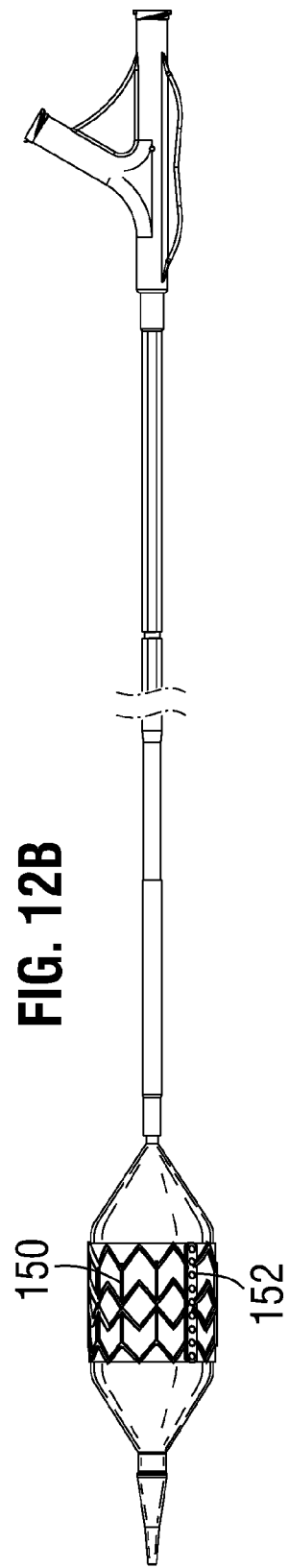
FIG. 12A
FIG. 12B

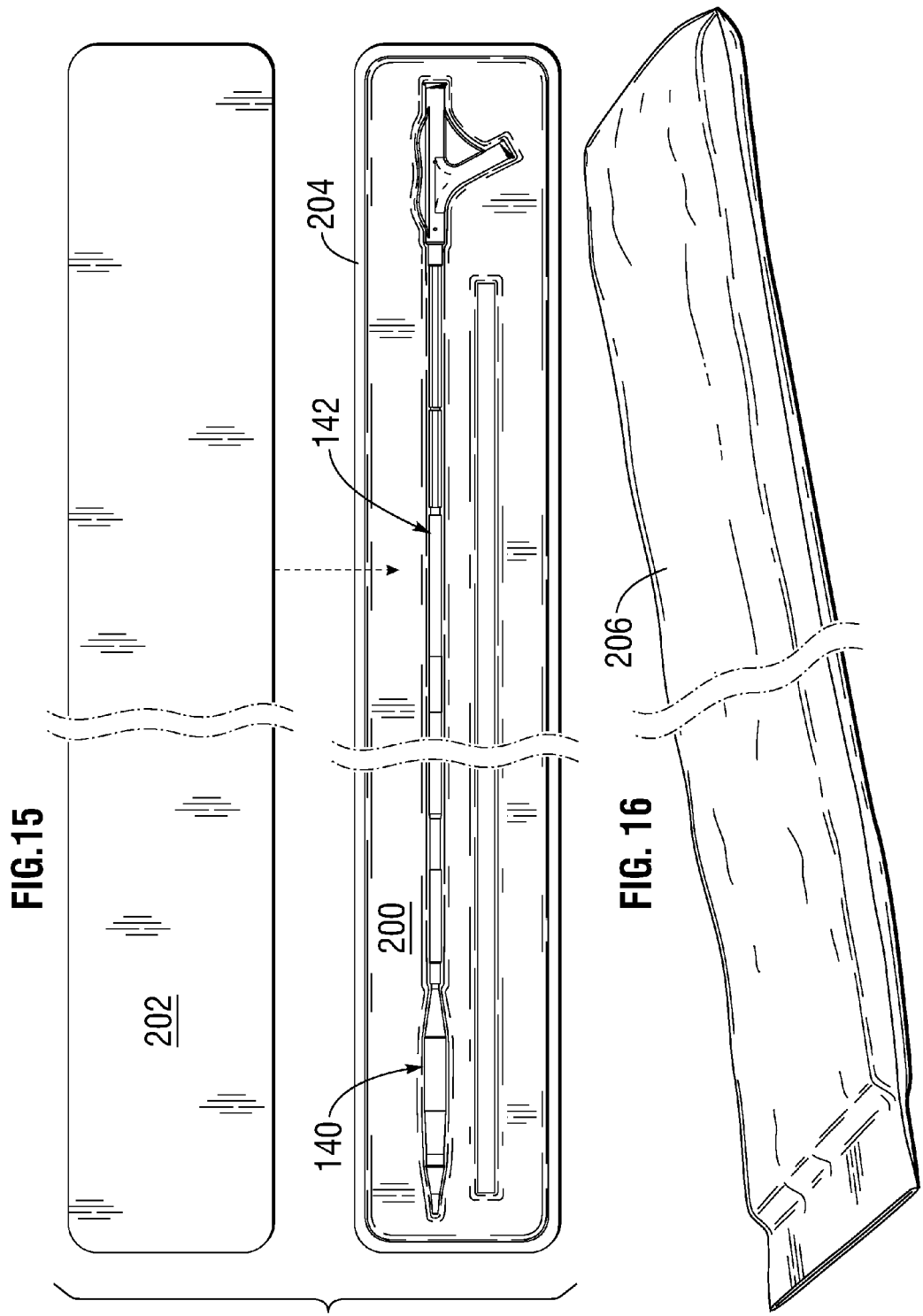

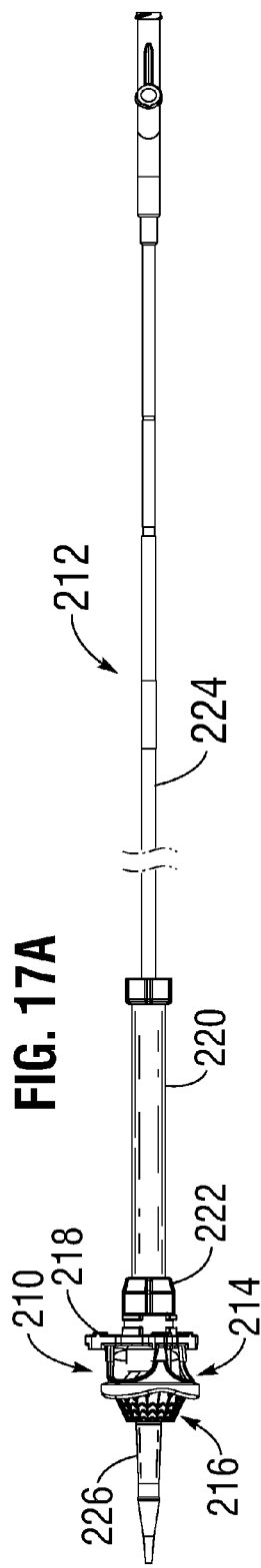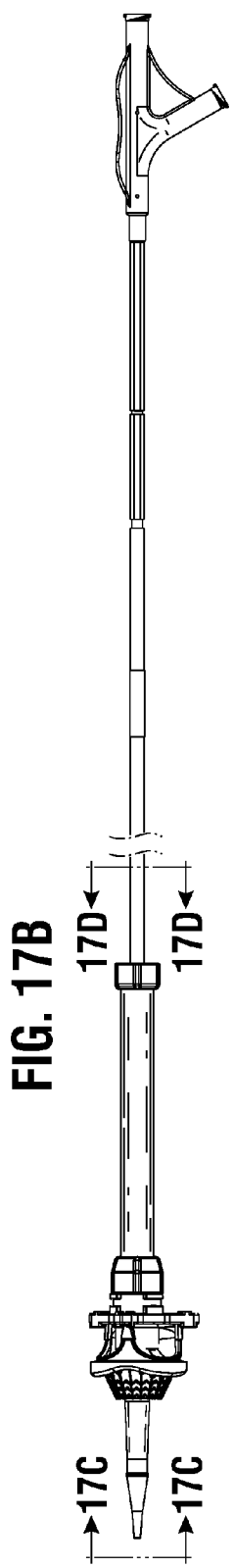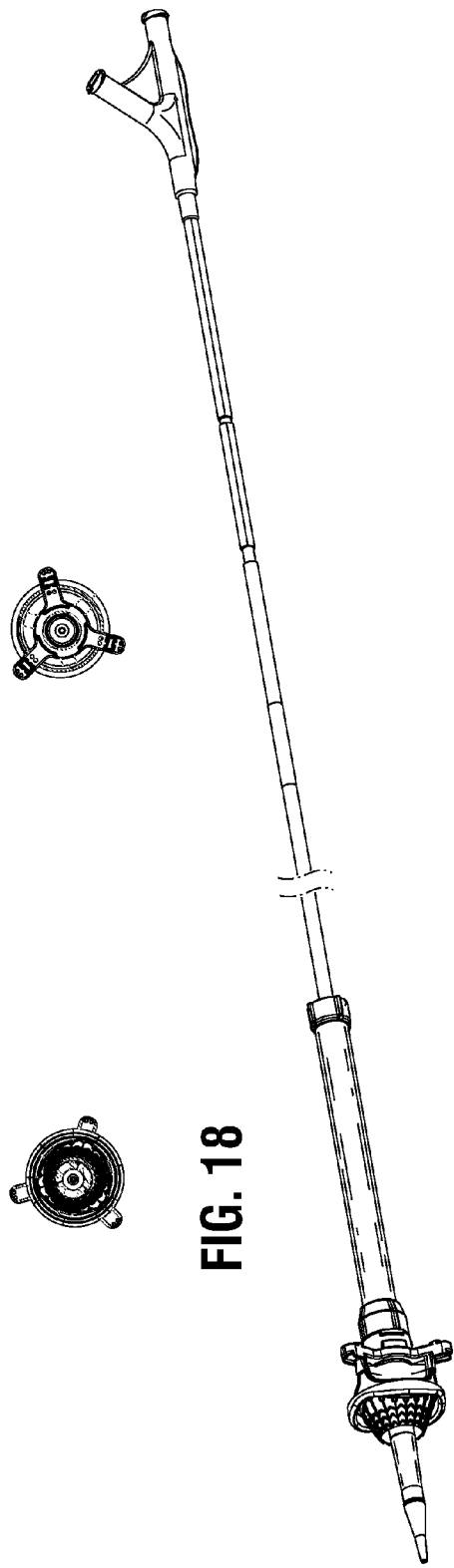

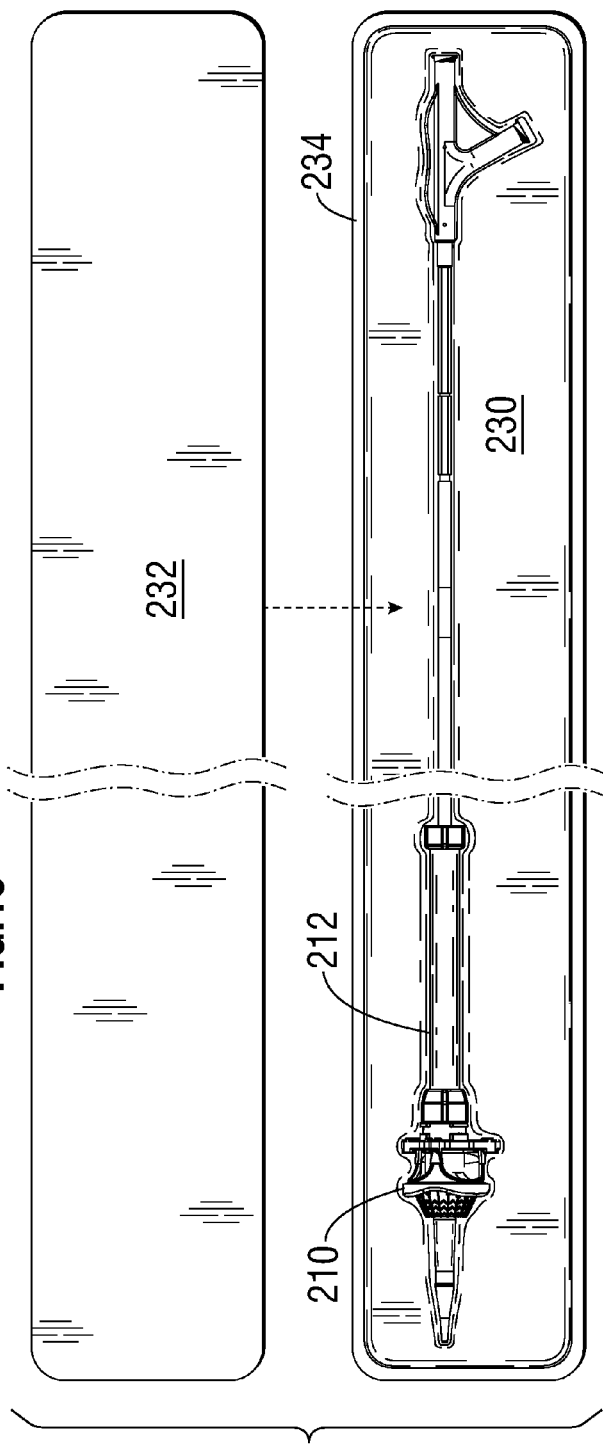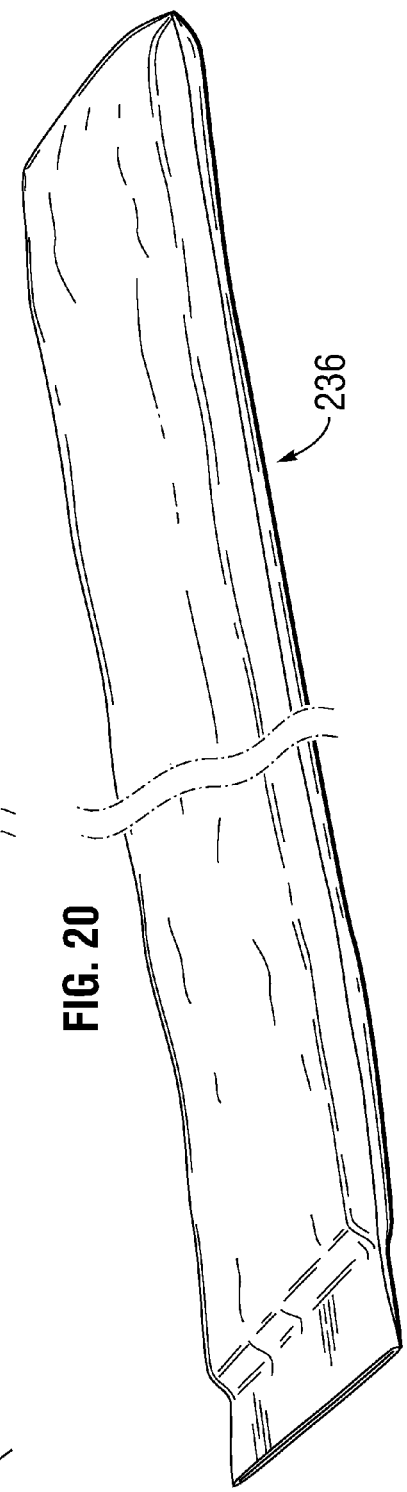

PROSTHETIC HEART VALVE DELIVERY SYSTEMS AND PACKAGING

RELATED APPLICATIONS

The present application claims priority under 35 U.S.C. §119 to U.S. Provisional Application No. 61/423,785, filed Dec. 16, 2010.

FIELD OF THE INVENTION

The present invention generally relates to methods of packaging prosthetic heart valves and, more particularly, to assemblies and methods for sterile storage of dry prosthetic heart valves and their delivery systems.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually. About one-half of these patients receive bioprosthetic heart valve replacements, which utilize biologically derived tissues for flexible fluid occluding leaflets.

The most successful bioprosthetic materials for flexible leaflets are whole porcine valves and separate leaflets made from bovine pericardium stitched together to form a tri-leaflet valve. The most common flexible leaflet valve construction includes three leaflets mounted to commissure posts around a peripheral support structure with free edges that project toward an outflow direction and meet or coapt in the middle of the flowstream. A suture-permeable sewing ring is provided around the inflow end.

Bioprosthetic heart valves are conventionally packaged in jars filled with preserving solution for shipping and storage prior to use in the operating theater. To minimize the possibility of damage to the relatively delicate bioprosthetic heart valves, they are stabilized with bracketing structure to prevent them from striking the inside of the jar. Prior to implantation in a patient, the valve is removed from the jar and then rinsed in a shower or immersed and agitated in a saline bath. Prosthetic valves typically have a valve holder centrally located and sutured thereto—to the inflow sewing ring for mitral valves and to the outflow commissure tips for aortic valves.

Glutaraldehyde is widely used as a storage solution due to its sterilant properties but is known to contribute to calcification. Strategies to incorporate chemicals to block or minimize unbound glutaraldehyde residues in the final product have been demonstrated to mitigate in vivo calcification.

One such strategy is to dehydrate the bioprosthetic tissue in a glycerol/ethanol mixture, sterilize with ethylene oxide, and package the final product "dry." This process eliminates the potential toxicity and calcification effects of glutaraldehyde as a sterilant and storage solution. There have been several methods proposed to use sugar alcohols (i.e., glycerine), alcohols, and combinations thereof as post-glutaraldehyde processing methods so that the resulting tissue is in a "dry" state rather than a wet state with excess glutaraldehyde. Glycerol-based methods can be used for such storage, such as described in Parker et al. (Thorax 1978 33:638). Likewise, U.S. Pat. No. 6,534,004 (Chen et al.) describes the storage of bioprosthetic tissue in polyhydric alcohols such as glycerol. In processes where the tissue is dehydrated in an ethanol/glycerol solution, the tissue may be sterilized by ethylene oxide (ETO), gamma irradiation, or electron beam irradiation.

More recently, Dove, et al. in U.S. Patent Publication No. 2009/0164005 propose solutions for certain detrimental changes within dehydrated tissue that can occur as a result of oxidation. Dove, et al. propose permanent capping of the aldehyde groups in the tissue (reductive amination). Dove, et al. also describe the addition of chemicals (e.g. antioxidants) to the dehydration solution (e.g., ethanol/glycerol) to prevent oxidation of the tissue during sterilization (ethylene oxide, gamma irradiation, electron beam irradiation, etc.) and storage.

In view of the development of dry tissue heart valves, opportunities for alternative packaging for such valves arise that will save money and facilitate deployment in the operating field.

SUMMARY OF THE INVENTION

The present application discloses methods of sterile packaging for dry bioprosthetic heart valves in combination with their delivery systems. New tissue treatment technology allows for packaging the tissue valves without liquid glutaraldehyde in a dry package. A double sterile barrier package disclosed herein contains, protects and preserves the dry bioprosthesis during ETO sterilization, transit and storage.

A system for packaging a dry tissue heart valve and its delivery system disclosed herein includes a dry tissue heart valve coupled to its valve delivery system. A primary container sized to receive the dry tissue heart valve coupled to its delivery system has a gas-permeable seal. A secondary container sized to receive the primary container is made of a gas-impermeable material and has a dual seal including a gas-permeable seal and a gas-impermeable seal. The primary container may comprise a flexible pouch or a relatively rigid tray. Likewise, the secondary container may comprise a flexible pouch or a relatively rigid tray. In one embodiment both the primary and secondary containers comprise relatively rigid trays. The secondary container may comprise a non-gas permeable foil label seal or foil pouch. The secondary container may also contain a dessicant.

In accordance with one embodiment, the valve delivery system includes a collapsible handle, which may have telescoping sections. Desirably, the telescoping sections include gas flow apertures open to interior lumens. In another embodiment, the prosthetic heart valve is expandable, and the delivery system includes a balloon catheter. Alternatively, the prosthetic heart valve has a non-expandable valve portion and an expandable stent, and the delivery system includes a balloon catheter.

Another method disclosed herein is for packaging a dry tissue heart valve, and comprises the steps of:
  providing a primary container having a gas-permeable seal;
  placing a dry tissue heart valve and its delivery system in the primary container and closing the gas-permeable seal;
  limiting movement of the heart valve in the primary container while providing gas flow passages around the heart valve;
  placing the sealed primary container with heart valve and delivery system therein into a secondary container made of a gas-impermeable material and sealing the secondary container with a gas-permeable seal to form a dual barrier assembly;

subjecting the dual barrier assembly to gas-based sterilization; and applying a gas-impermeable seal to the secondary container to prevent oxygen or water from passing therethrough.

In the aforementioned method, the step of subjecting comprises exposing the dual barrier assembly to ethylene oxide (ETO) gas. In accordance with a preferred embodiment, the primary container is a tray having an upper surface and a cavity surrounded by an upper rim and descending downward therefrom, the tray being made of gas-impermeable material, wherein the dry tissue heart valve and its delivery system are placed in the tray cavity. Further, the step of sealing the tray includes covering the tray upper surface with a gas-permeable lid. The secondary container may be a second tray having an upper surface and a cavity surrounded by an upper rim and descending downward therefrom. The second tray is made of gas-impermeable material and the cavity is sized to receive the first tray, and the gas-impermeable seal is a gas-impermeable label sealed to the upper rim of the second tray. In one embodiment, the second tray comprises a double flanged upper rim, and further includes a gas-permeable lid sealed to an inner flange and the gas-impermeable label sealed to an outer flange. Or, the secondary container may be a flexible pouch including a gas-impermeable seal, and the pouch may also include a gas-permeable seal inside of the gas-impermeable seal.

In accordance with one embodiment of the present application, a system for handling a heart valve includes a prosthetic heart valve, a heart valve delivery system, and a valve holder removably secured to the prosthetic heart valve. The heart valve delivery system features a collapsible handle with a series of concentric telescoping sections, the handle having a collapsed state and an elongated state. A distal telescoping section of the handle has a locking head projecting in a distal direction. The valve holder includes a handle coupler extending in a proximal direction and having structure sized and shaped to mate with the locking head of the handle so that the prosthetic heart valve extends distally from the distal telescoping section of the handle. In a preferred embodiment, the telescoping sections are generally tubular and gradually enlarge in diameter from the distal telescoping section to a proximal telescoping section. A proximal telescoping section desirably has an ergonomic grip with undulations for receiving fingers of a user.

In one embodiment, the telescoping sections include interfering lips that prevent any one section from passing completely within another section and that prevent the sections from disengaging past the elongated state. The system may further include elastomeric seals between adjacent telescoping sections to provide frictional tightness between the telescoping sections. The locking head is preferably elastomeric and the structure on the handle coupler sized and shaped to mate with the locking head comprises an internal cavity into which the elastomeric locking head closely fits. Desirably, all but a proximal telescoping section include outwardly directed sealing sections on proximal ends thereof, and all but the distal telescoping section include an inwardly-directed lip on distal ends thereof and an inwardly-directed circular feature spaced closely from distal ends thereof. Converting the handle to the elongated state locks each sealing section in a region between the inwardly-directed lip and the inwardly-directed circular feature of the adjacent telescoping section.

The system is particularly useful for handling dry prosthetic tissue valves. The system may further include storage containers for the prosthetic heart valve, heart valve delivery system, and valve holder. For instance, a primary container is sized to receive the heart valve coupled to its holder and the delivery system with the handle in its collapsed state, the primary container having a gas-permeable seal. A secondary container is sized to receive the primary container, the secondary container being made of a gas-impermeable material and having a dual seal including a gas-permeable seal and a gas-impermeable seal. The telescoping sections may include gas flow apertures open to interior lumens to permit good flow during gas sterilization.

Another method for handling a heart valve comprises first procuring a sterile package containing a prosthetic heart valve removable secured to a valve holder. The holder is coupled to a heart valve delivery system having a collapsible handle with a series of concentric telescoping sections. The handle has a collapsed state with a first length and an elongated state with a second length relatively longer than the first length, and the handle is contained in the sterile package in its collapsed state. The method includes removing the valve, holder and handle from the sterile package, converting the handle from its collapsed state to its elongated state, including pulling the telescoping sections to lengthen the handle until adjacent telescoping sections lock together, and delivering and implanting the prosthetic heart valve.

In the preceding method, the telescoping sections are preferably generally tubular and gradually enlarge in diameter from a distal telescoping section to a proximal telescoping section, and wherein the proximal telescoping section has an ergonomic grip with undulations for receiving fingers of a user. The telescoping sections may include interfering lips that prevent any one section from passing completely within another section and that prevent the sections from disengaging past the elongated state. Desirably, elastomeric seals are provided between adjacent telescoping sections to provide frictional tightness between the telescoping sections. In a preferred embodiment, all but a proximal telescoping section include outwardly directed sealing sections on proximal ends thereof, and all but a distal telescoping section include an inwardly-directed lip on distal ends thereof and an inwardly-directed circular feature spaced closely from distal ends thereof, wherein converting the handle to the elongated state locks each sealing section in a region between the inwardly-directed lip and the inwardly-directed circular feature of the adjacent telescoping section. The distal telescoping section of the handle preferably has a locking head projecting in a distal direction and the valve holder includes a handle coupler extending in a proximal direction and having structure sized and shaped to mate with the locking head of the handle so that the prosthetic heart valve extends distally from the distal telescoping section of the handle. Further, the locking head is preferably elastomeric and the structure on the handle coupler sized and shaped to mate with the locking head comprises an internal cavity into which the elastomeric locking head closely fits.

The handling method is particularly useful for dry prosthetic tissue valves and the sterile package contains no liquid preservative. The sterile container may include a primary container and a secondary container, the primary container having a gas-permeable seal and providing gas flow passages therewithin around the heart valve, the sealed primary container being placed within the secondary container. The secondary container includes a dual seal with a gas-permeable seal inside of a gas-impermeable seal capable of preventing oxygen or water from passing therethrough. The method further includes removing the gas-impermeable seal from the secondary container and subjecting the sterile container to gas-based sterilization, removing the gas-permeable seal from the secondary container, removing the gas-permeable seal from the primary container, and performing the step of removing the valve, holder and handle from the sterile package. Preferably, the primary container is a tray having an upper surface and a cavity surrounded by an upper rim and descending downward therefrom, the tray being made of gas-impermeable material, wherein the dry tissue heart valve and its delivery system are placed in the tray cavity. In one embodiment, the secondary container comprises a flexible pouch.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1 is a perspective assembled view of an exemplary dry prosthetic heart valve connected to its delivery system in an extended configuration;

FIG. 2 is an exploded perspective view of the components of the prosthetic heart valve and delivery system of FIG. 1;

FIG. 3 is a longitudinal sectional view of the assembled prosthetic heart valve and delivery system of FIG. 1;

FIGS. 4A-4C are elevational and opposite end views of the assembled prosthetic heart valve and delivery system of FIG. 1 in its extended configuration;

FIG. 5A is an elevational view similar to FIG. 4A but rotated 90°, and FIG. 5B is the same as FIG. 5A but with the heart valve delivery system in a collapsed configuration;

FIG. 6A is an elevational view similar to FIG. 5A but showing internal features in phantom;

FIG. 6B is a longitudinal sectional view of the heart valve and extended delivery system of FIG. 6A taken along line 6B-6B, and FIG. 6C is a detailed view thereof;

FIG. 7 is a longitudinal sectional view of the heart valve and extended delivery system as in FIG. 6B with the delivery system collapsed;

FIG. 8A is an elevational view of an alternative heart valve delivery system showing internal features in phantom;

FIG. 8B is a longitudinal sectional view of the heart valve and delivery system of FIG. 8A taken along line 8B-8B;

FIG. 9 is a longitudinal sectional view of the heart valve and extended delivery system as in FIG. 8B with the delivery system collapsed;

FIGS. 12A-12B are broken plan views of an expandable prosthetic heart valve and its delivery system in both collapsed and expanded configurations;

FIG. 15 is an exploded plan view of the expandable prosthetic heart valve and delivery system as in FIG. 12A mounted in an exemplary primary storage container in the form of a tray;

FIG. 16 is a perspective view of the prosthetic heart valve and delivery system in the tray as in FIG. 15 contained within a secondary storage container in the form of a pouch;

FIGS. 17A-17D and 18 are broken elevational and perspective views of a hybrid prosthetic heart valve and its delivery system;

FIG. 19 is an exploded plan view of the hybrid prosthetic heart valve and delivery system as in FIG. 17B mounted in an exemplary primary storage container in the form of a tray;

FIG. 20 is a perspective view of the hybrid prosthetic heart valve and delivery system in the tray as in FIG. 19 contained within a secondary storage container in the form of a pouch;

DETAILED DESCRIPTION OF THE PREFERRED EMBODIMENTS

Figure 10:
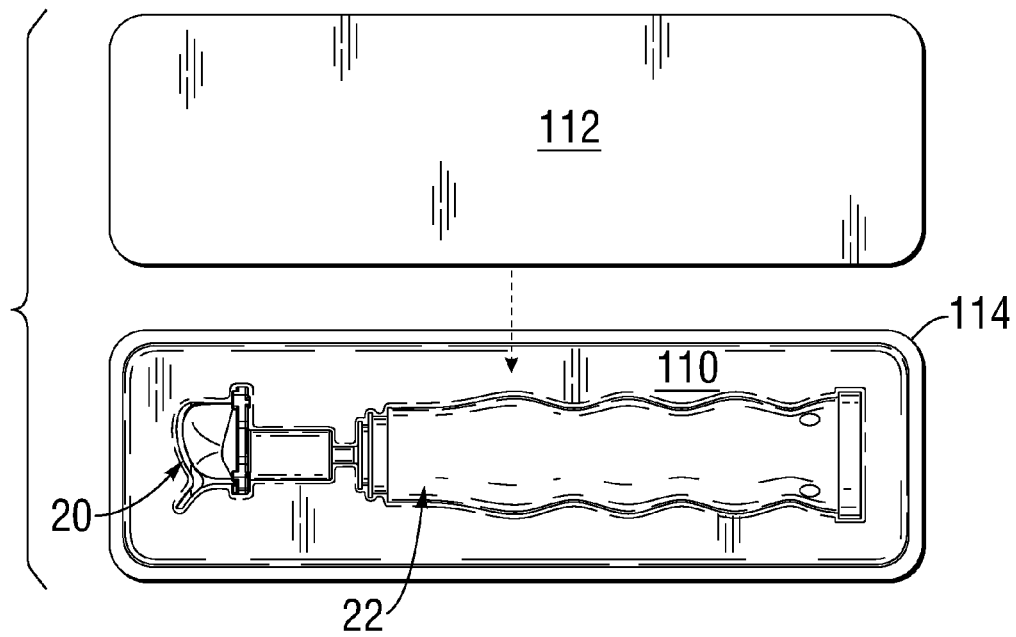
FIG. 10 is an exploded plan view of a prosthetic heart valve and collapsed delivery system as in FIG. 5B mounted in an exemplary primary storage container in the form of a tray.

The present invention provides improved packaging systems for dry prosthetic heart valves and their delivery systems that provides an efficient vehicle for gas sterilization, and prevents oxidation of the valve during long-term storage. The packaging systems for storing dry prosthetic tissue heart valves do not require liquid containment.

The present application provides techniques for storing bioprosthetic heart valves, in particular valves that have been dried and are not stored immersed in a preservative solution. The term "dried" or "dry" bioprosthetic heart valves refers simply to the ability to store those heart valves without the preservative solutions. There are a number of proposed methods for drying bioprosthetic heart valves, and for drying tissue implants in general, and the present application provides a storage solution for bioprosthetic heart valves that are processed by any of these methods. A particularly preferred method of drying bioprosthetic heart valves is disclosed in U.S. Patent Publication No. 2008/0102439 to Tian, et al. An alternative drying method is disclosed in U.S. Pat. No. 6,534,004 to Chen, et al. Again, these and other methods for drying bioprosthetic heart valves may be used prior to implementing the storage techniques described herein.

A number of exemplary bioprosthetic heart valves and their delivery systems are shown and described in the present application. Each of these different types of heart valves may be processed so that they are stored dry. The reader will understand that the present methodologies apply to any and all bioprosthetic heart valves that are stored dry, and are not limited to those exemplary valves shown herein. In particular, prosthetic heart valves for implant at any of the four native valve annuluses—aortic, mitral, pulmonary, and tricuspid—may be dried and stored in accordance with the principles described herein.

Additionally, a number of techniques for packaging the dry bioprosthetic heart valves and their delivery systems are illustrated and described herein, though these techniques can also apply to other packaging configurations. In general, a bioprosthetic heart valve must be stored in sterile conditions, which requires at least one sterile container. Preferably, however, a dual-barrier packaging system is used to reduce the chance of contamination of the implant at the time of surgery.

FIG. 1 illustrates an exemplary dry prosthetic heart valve 20 connected to a telescoping delivery system 22 in an extended configuration, while FIG. 2 shows the components, and FIG. 3 is a longitudinal sectional view of the assembly.

The heart valve 20 comprises a plurality, preferably three, of flexible leaflets 24 that are mounted to a peripheral stent structure 26 and form fluid occluding surfaces within the valve orifice to form a one-way valve. The stent structure 26 includes a plurality of generally axially extending commissures 28 circumferentially distributed around the valve between and in the same number as the number of leaflets 24. Although not shown, additional components of the heart valve 20 typically include an inner stent and/or wireform support structure that provide a structural skeleton surrounding an inflow orifice and extending up the commissures 28. The inner components of the heart valve 20 may be made of suitable metal or plastic. As is well known, adjacent flexible leaflets 24 connect to and extend upward to meet along each of the commissures 28. In the illustrated embodiment, the structural components of the heart valve 20 support each flexible leaflet 24 along a valve cusp 30 and along two commissure 28 edges. A free edge of each leaflet 24 extends inward toward a central flow orifice and coapts, or mates, with the free edges of the other leaflets, as shown. The valve orifice is oriented around an axis along an inflow-outflow direction through the valve. The valve commissures 28 project in the outflow direction, with the convex valve cusps 30 extending in the inflow direction between adjacent commissures. Although not shown, bioprosthetic heart valves often include on the inflow end a sewing ring that conforms to the undulating contours of the valve cusps, or defines a generally circular, planar ring. The present application should not be considered limited to a particular valve construction unless explicitly stated herein.

The flexible leaflets 24 may be made from a variety of bioprosthetic tissue, such as bovine pericardium where the individual leaflets 24 are cut from pericardial sac of a cow. Some recent valves include conditioned leaflets 24 where the thickness of individual leaflets varies at different points, such as being thinner in the middle and thicker around the edges where sutures pass. Techniques such as compression of the pericardium, laser shaving or mechanical skiving may be utilized. An exemplary dry tissue heart valve that may be stored without need for liquid preservatives in the packaging systems described herein may be obtained from Edwards Lifesciences of Irvine, Calif. One preferred tissue treatment process includes applying a calcification mitigant such as a capping agent or an antioxidant to the tissue to specifically inhibit oxidation in dehydrated tissue and reduce in vivo calcification. In one method, tissue leaflets in assembled bioprosthetic heart valves are pretreated with an aldehyde capping agent prior to dehydration and sterilization. Exemplary processes are described in U.S. Patent Application No. 2009-0164005 to Dove, et al., filed Jun. 25, 2009, the disclosure of which is expressly incorporated herein by reference.

As mentioned above, the heart valve 20 is representative of any number of bioprosthetic heart valves, though the one shown is most suited for aortic annulus implant. In particular, the outflow commissures 28 of the valve 20 are secured to a holder 40 on the distal end of the delivery system 22. The illustrated holder 40 has three legs that extend radially outward from a central hub into proximity with the tips of the valve commissures 28 and are secured thereto, though alternatively the holder may have legs that angle outward and axially and couple to the mid-point of the valve cusps 30.

In the orientation shown, the valve 20 is advanced with its inflow end leading. Because most conventional aortic valve deliveries are accomplished through the ascending aorta down to the aortic annulus, the inflow end is the leading or distal end (away from the user) in terms of the delivery orientation. Of course, alternative aortic valve delivery orientations are possible, such as transapically through the left ventricular apex to the aortic annulus. In the same manner, conventional mitral valve deliveries are typically accomplished through the left atrium with the outflow end and commissures 28 as the leading or distal end in terms of the delivery orientation. Thus, for example, a representative mitral heart valve would have its inflow end mounted to the holder and its commissures projecting distally, or to the left in the sense of FIG. 1.

Likewise, the particular delivery system 22 exemplifies many delivery systems, which typically include the holder 40 and an elongated handle for manipulation by the surgeon. For instance, many conventional systems utilize a simple elongated rod which may or may not be bendable and which includes a distal male threaded end which couples to a female threaded socket in the holder 40. The exemplary delivery system 22 is particularly well-suited to the storage techniques described herein because it can be collapsed from its extended configuration shown in FIG. 1. It is important to understand, however, that although the exemplary telescoping delivery system 22 has distinct advantages, such an economical and intuitive design, it may be replaced by other such collapsible systems. For example, rather than having telescoping sections, the delivery system 22 may be foldable like a pocket knife, or constructed with a scissor-like or accordion-style extender mechanism. Those of skill in the art will understand there are numerous ways for converting a delivery system from the elongated configuration shown in FIG. 1 to the collapsed configuration shown in FIG. 5B. The present application contemplates storage of bioprosthetic heart valves with any number of delivery systems, and the principles described herein should not be considered limited to any particular system unless excluded by the claim language.

During implant, the surgeon manipulates the extended delivery system 22 and advances the heart valve 20 into implant position at the target annulus. Once in position, and typically after anchoring sutures have been deployed between a sewing ring (not shown) and the surrounding native annulus, the surgeon severs the attachment sutures coupling the holder 40 to the valve 20, and removes the delivery system 22.

Now with reference to FIGS. 1-7, elements of the exemplary telescoping delivery system 22 will be described. The system 22 includes a large proximal grip section 50 having a proximal end cap 52. In the illustrated embodiment, the grip section 50 features an undulating exterior contour which allows for better handling and gripping during manipulation of the telescoping components and by the surgeon during valve delivery, such as featuring an ergonomic grip with undulations for receiving fingers of the surgeon. The grip section 50 is substantially tubular and a distal end 54 thereof mates around a proximal end 56 of a tubular intermediate section 58. The outer diameter of the intermediate section 58 is sized to fit closely within the lumen 60 of the grip section 50. In the same manner, a distal end 62 of the intermediate section 58 mates around a proximal end 64 of a cylindrical distal section 66. The outer diameter of the distal section 66 is sized to fit closely within the lumen 68 of the intermediate section 58. For purposes of reducing weight and maintaining balance along the length of the telescoping delivery system 22, the distal section 66 is also desirably tubular having an inner lumen 70. The distal end of the distal section 66 includes a faceplate 72 from which projects in a distal direction a plunger rod 74 and locking head 76, the function of which will be described below.

The main components of the telescoping delivery system 22—the grip, intermediate, and distal sections—are desirably made of a lightweight and rigid polymer such as ABS (Acrylonitrile-Butadiene-Styrene), though any lightweight material suitable for surgical use may be used. More particularly, materials for the delivery system components may be a heat-extruded or injection-molded polymer, or machined stainless steel, cobalt chrome, Nitinol, or other metal alloy. The plunger rod 74 is also made of a rigid polymer, such as ABS, though the locking head 76 is desirably formed of an elastomeric material such as silicone rubber. Likewise, a pair of O-ring seals 78 interposed between the telescoping sections are each formed of an elastomeric material such as silicone. The O-ring seals 78 provide a degree of frictional tightness between the telescoping sections that rigidifies the elongated assembly to facilitate manipulation of the heart valve 20 during delivery, though using silicone adds lubricity and therefore smoothes relative sliding of the sections.

Referring to the exploded view of FIG. 2 and sectional views in FIGS. 3, 6B and 6C, interaction between the main telescoping components 50, 58, and 66 is now described. The distal ends 54, 62 of the two larger sections—the grip section 50 and intermediate section 58, respectively—both include inwardly-directed lips 80 that interfere with outwardly-directed lips 82 on the proximal ends 56, 64 of the intermediate section 58 and distal section 66, respectively. These interacting lips 80, 82 prevent the three sections from disengaging past the elongated configuration shown in the figures. In addition, the distal ends 62, 72 of the two smaller sections—the intermediate section 58 and distal section 66—have outwardly-directed flanges 84 that interfere with the distal ends 54, 62 of the grip section 50 and intermediate section 58, respectively. These outwardly-directed flanges 84 prevent each of the two smaller sections from sliding completely into the cavities of the adjacent larger section. It should be noted that the difference in diameters is slight and lead-in ramps may be provided on one or both of each pair of interfering flanges so that the cooperating sections can be fit together with minimal force during assembly.

FIG. 2 best shows a pair of sliding sealing sections formed on the proximal ends of the intermediate section 58 and distal section 66. More particularly, the sealing sections include, on the exterior of the sections 58, 66, annular recessed regions 86 which are created between the respective proximal ends 56, 64 and outwardly-directed circular flanges 88. The elastomeric O-rings 78 fit closely within the recessed regions 86, as seen in the detail view of FIG. 6C. The outer diameter of the O-rings 78 is slightly larger than the inner diameter of the lumen of the respective mating section so that a frictional interference is created. Each of the two larger sections 50, 58 include a series of inwardly-directed circular feature 90 such as a series of rounded bumps or a continuous circular rib as shown projecting inwardly from their respective lumens 60, 68. The axial length of the sealing sections that receive the O-rings 78 is approximately the same as the axial distance between the circular feature 90 and the respective distal ends 54, 62 of the larger sections 50, 58. This can be seen in FIG. 6C. When the sections are extended, as seen in FIG. 1, the sealing sections lock in the region between the circular feature 90 in the distal ends of the sections 50, 58, thus maintaining the extended configuration. However, the circular feature 90 is rounded and equal or just smaller in diameter than the outer diameters of the circular flanges 88 and proximal ends 56, 64, thus permitting the sections to be extended beyond a tensile force threshold and collapsed beyond a threshold of compressive force. The threshold of tensile force will be set in a level that enables easy extension of the system 22, but the compressive threshold will be calibrated so that it is larger than the force expected during valve delivery. Thus, the system 22 can be extended fairly easily and remains in that configuration during use.

With reference now to FIG. 2, and the sectional view of FIG. 3, the valve holder 40 includes three outwardly-directed legs 100 shaped and dimensioned to mate with the commissures 28 of the valve 20. Typically, the commissures are covered with fabric, and sutures are used to connect the legs 100 thereto. As mentioned above, in an alternative embodiment the legs 100 may be longer and angled in the axial direction so as to contact the cusps 30 of the valve 20. Various other holder arrangements are known.

The holder 40 further includes a cylindrical handle coupler 102 extending in a proximal direction. As seen in FIGS. 6B and 7, the handle coupler 102 defines two inner cavities—a larger proximal cavity 104 and a smaller distal cavity 103. The distal cavity 103 is sized and shaped approximately the same as the locking head 76 on the distal end of the delivery system 22. A narrow neck region 106 between the cavities 103, 104 has an inner diameter smaller than the outer diameter of the locking head 76.

In use, the prosthetic heart valve 20 and delivery system 22 are packaged in the collapsed configuration of FIGS. 5B and 7. As seen in FIG. 7, the locking head 76 resides within the larger proximal cavity 104 during storage. Just prior to the valve implant procedure, a technician pushes the entire delivery system 22 in its collapsed configuration toward the coupler 102, as seen by the arrow on plunger rod 74, so that the elastomeric locking head 76 forces past the narrow neck 106 and fits tightly into the smaller distal cavity 103. Subsequently, the technician pulls the grip section 50 away from the coupler 102 to extend the telescoping sections 50, 58, as seen by the arrows to the right, until the O-rings 78 travel past the circular feature 90, as seen in FIG. 6B. The system is now effectively locked in its extended configuration ready for use.

FIGS. 8A-8B and 9 illustrates a slight modification to the delivery system 22. In particular, a locking head 76' has a tapered, somewhat bullet shape, as does the smaller distal cavity 103' defined within the coupler 102'. The tapered nature of the locking head 76' facilitates passage through the narrow neck region 106.

FIG. 10 illustrates an exemplary primary storage container for the prosthetic heart valve 20 and collapsed delivery system 22 as seen in FIG. 5B. The primary storage container comprises a molded storage tray 110 and a sheet-like gas-permeable lid 112. In particular, the assembled heart valve 20 and delivery system 22 are placed within a cavity of the storage tray 110, whereupon the lid 112 is adhered to an upper rim 114 of the tray. The upper rim 114 defines the tray upper surface, and the process of adhering the lid 112 to the rim 114 can be performed easily using automated equipment. The adhesive may be provided on the upper rim 114, or on the underside of the lid 112. In a preferred embodiment, inwardly-directed features (not shown) provided in the cavity of the tray 110 secure the heart valve 20 and delivery system 22 from movement therein. Preferably, these features engage with a snap or tactile feedback. Because the tray 110 secures the components in this manner, the heart valve 20 is stably suspended within the cavity without touching the sides of the tray 110.

Preferably, the lid 112 is closely dimensioned to the perimeter of the upper rim 114, and the band of adhesive is a pressure-seal or a heat seal adhesive to facilitate sealing under pressure and/or temperature. The material of the lid 112 is breathable, or gas-permeable, to permit gas sterilization of the contents sealed within the tray 110, in particular the dry tissue heart valve 20. One suitable gas-permeable material is a sheet of high-density polyethylene fibers, which is difficult to tear but can easily be cut with scissors. The material is highly breathable and water vapor and gasses can pass through the fibers, but not liquid water. For instance, various Tyvek materials from DuPont may be used. Also, exemplary hot-melt adhesives used to secure the lid 112 to the tray 110 may be obtained from Perfecseal or Oliver-Tolas, for example. Such a material permits sterilization of the tray contents using Ethylene Oxide (ETO), which gradually passes through the lid 112 to the interior tray. The lid 112 presents a sterile barrier and prevents ingress of microorganisms. The tray 110 is a gas-impermeable molded material, such as a polyethylene terephthalate copolymer (PETG). Various medical storage materials and packaging suitable for assembly of components of the present application are available from companies such as Dupont, Perfecseal, Oliver-Tolas, and Mangar. Other means of sterilization include gamma irradiation or electron beam irradiation.

Ethylene oxide (ETO), also called oxirane, is the organic compound with the formula $C_2H_4O$. It is commonly handled and shipped as a refrigerated liquid. ETO is often used as sterilant because it kills bacteria (and their endospores), mold, and fungi. It is used to sterilize substances that would be damaged by high temperature techniques such as pasteurization or autoclaving. Ethylene oxide is widely used to sterilize the majority of medical supplies such as bandages, sutures, and surgical implements in a traditional chamber sterilization method, where a chamber has most of the oxygen removed (to prevent an explosion) and then is flooded with a mixture of ethylene oxide and other gases that are later aerated.

Certain features of the delivery system 22 and tray 110 facilitate gas sterilization, such as with ETO, though other means such as gamma irradiation or electron beam irradiation could be used. Specifically, the delivery system 22 provides gas flow passages for gas flow in and out of the various components. Good flow of sterilization gas through the components facilitates complete and rapid sterilization of the dry bioprosthetic tissue heart valve 20 and rapid removal of the residual ethylene oxide and ethylene chlorohydrin (ECH) residual gas. With reference to FIGS. 1-7, and in particular to FIG. 2, each of the telescoping sections 50, 58, 66 includes at least one, and preferably at least two, apertures 120 in their tubular side walls. Preferably, because the delivery system 22 is stored in its collapsed configuration as seen in FIG. 5B, the apertures 120 are located toward the proximal ends of the telescoping sections 50, 58, 66 so that the apertures of adjacent sections are not separated by the O-ring seals 78 and gas may flow into the concentric lumens of the sections. The apertures 120 permit passage of sterilization gas into the inner lumens of the components, which completely sterilizes all parts of the system. There are consequently no dead space cavities within the delivery system 22. Likewise, the tray 110 retains the heart valve 20 and delivery system 22 securely therein but provides adequate channeling in and around the components therein to eliminate any enclosed spaces. The sterilization gas can therefore flow evenly throughout the entire enclosure.

One advantage of the packaging solutions described herein is a double sterile barrier, wherein the inner and outer sterile containers allow for gas sterilization, such as with ETO, and with a second seal the outer sterile container also provides an oxygen barrier to the product after sterilization. The inner sterile container has been described above with reference to FIG. 10 in the form of a storage tray 110 sealed with the lid 112. The sealed storage tray 110 is received within a secondary or outer container and the dual barrier assembly is then sterilized, so that there are redundant sterile barriers. Subsequently, the dual barrier assembly is sealed to prevent oxygen from reaching the heart valve, thus preventing oxygenation and potentially reducing calcification after implant. In the exemplary packaging sequence, the primary and secondary containers are first assembled together and each closed with a gas-permeable barrier to form a dual barrier assembly which is gas-sterilized. Subsequently, the oxygen barrier is added, such as by converting the secondary container from being gas-permeable to being gas-impermeable. However, if the entire process is done in sterile conditions, such as in a clean room environment, the primary container may be closed and sterilized before being placed within the secondary container, which is then closed and sterilized. In other words, there may be one or two sterilization steps prior to sealing the entire assembly against oxygen ingress.

Desirably, a dessicant is used within the inner and/or the outer packaging layers. For instance, a dessicant pouch may be inserted with the heart valve and delivery system into the inner package, to absorb any residual water vapor trapped therein when the gas-permeable tray lid 112 is closed. A second dessicant pouch may be inserted between the inner and outer barriers to absorb any residual water vapor therein, or it may be the only dessicant pouch used.

The present application describes two different secondary barriers—one a storage tray similar to that described earlier, and the other a flexible pouch. The secondary barrier protects and preserves the primary sterile barrier package in a sterile environment, and prevents oxygen from reaching the heart valve within. A further outer shelf box may be used to facilitate temperature monitoring during distribution and storage, and protect the delicate implant from distribution hazards such as shock, impact and extreme temperatures.

Figure 11:
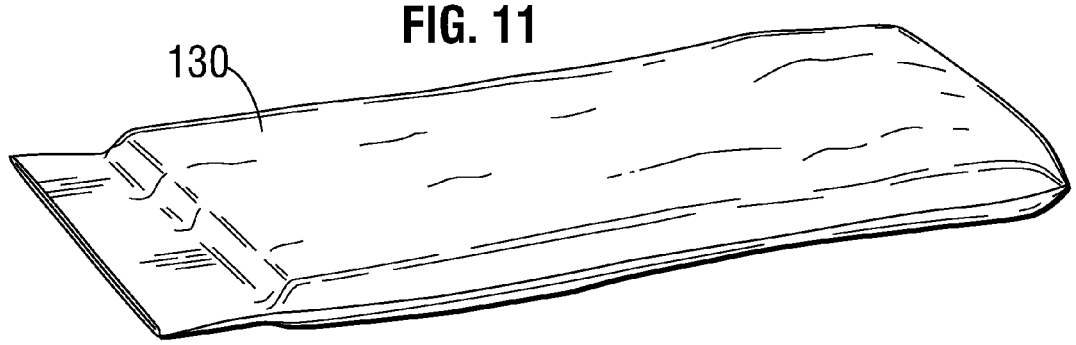
FIG. 11 is a perspective view of the prosthetic heart valve and delivery system in the tray as in FIG. 10 contained within a secondary storage container in the form of a pouch.

FIG. 11 is a perspective view of the prosthetic heart valve 20 and delivery system 22 in the primary storage tray 110 with the lid 112 attached (all not shown), as in FIG. 10, and then contained within a secondary storage container in the form of a pouch 130. Desirably, the storage pouch 130 includes a dual seal system on its open end which provides both a gas-permeable portion and a gas-impermeable portion, depending on which seal is closed. More detail on such a dual seal system will be provided below with reference to the embodiment shown in FIGS. 13-14.

FIGS. 12A-12B illustrate an expandable prosthetic heart valve 140 and its delivery system 142. Expandable prosthetic heart valves are known in the art, and the illustrated 140 is representative of a number of such valves which can be converted from a narrow constructed configuration to a wider expanded configuration. Typically, the valves are balloon expanded into position at a target annulus after having been advanced through the vasculature. The most common delivery routes commence at the femoral or carotid arteries, though other more direct routes through chest ports are also known. One particularly successful expandable prosthetic heart valve is the Edwards SAPIEN Transcatheter Heart Valve available from Edwards Lifesciences of Irvine, Calif. The Edwards SAPIEN valve may be placed either through a transfemoral (RetroFlex 3 Transfemoral Delivery System from Edwards Lifesciences) or transapical (Ascendra Transapical Delivery System from Edwards Lifesciences) approach. FIGS. 12A-12B illustrate a system much like the RetroFlex 3 Transfemoral Delivery System from Edwards Lifesciences.

The delivery system 142 includes an elongated catheter 144 having an expansion balloon 146 near a distal end thereof. The prosthetic heart valve 140 mounts around the balloon 146 and is expanded thereby. The system further includes proximal luer connectors 148 for delivery of balloon inflation fluid, passage of a guide wire, or other such functions. In the exemplary embodiment, the prosthetic heart valve 140 includes a plurality of balloon-expandable struts 150 in between three axially-oriented commissure bars 152. Bioprosthetic tissue mounts within the framework created by the struts 150 and bars 152, such as with supplementary fabric.

Figure 13:
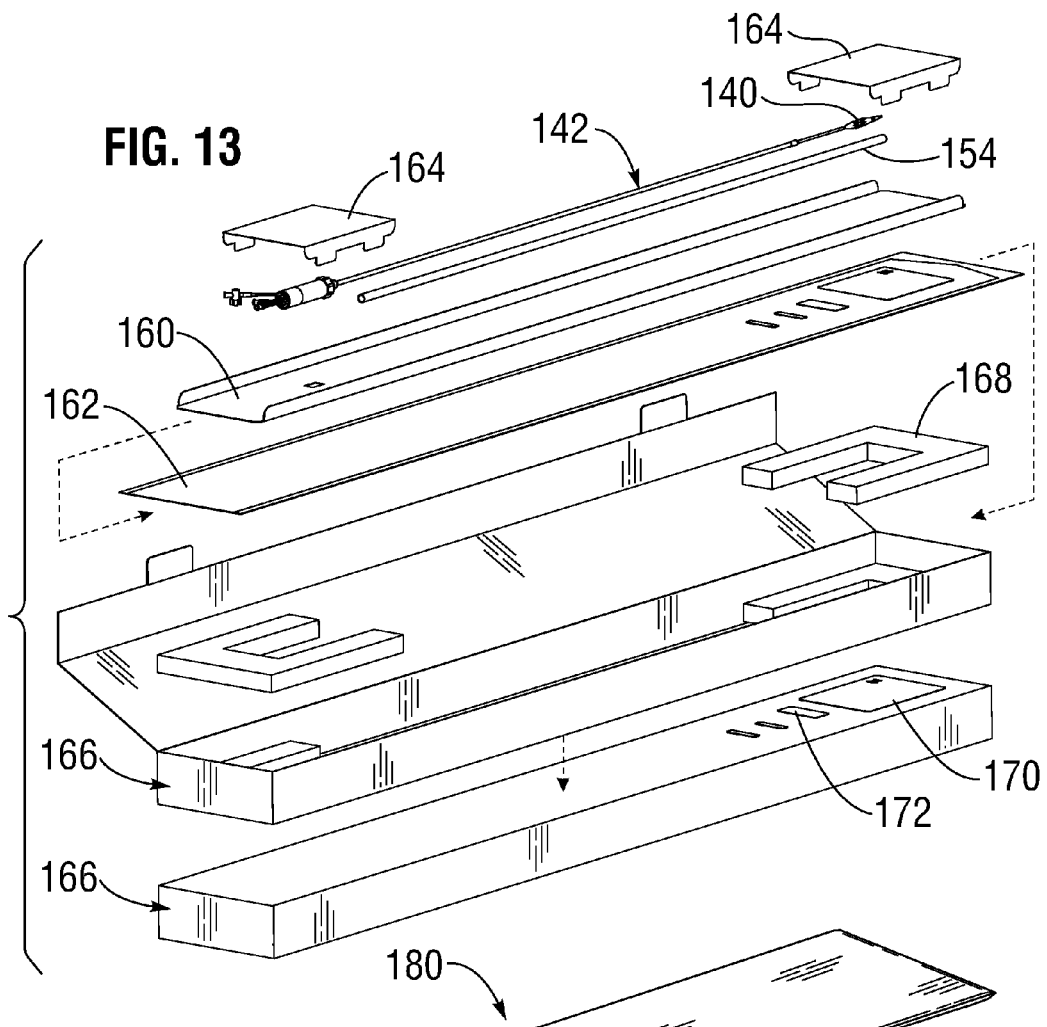
FIG. 13 is an exploded perspective view of the expandable prosthetic heart valve and delivery system as in FIG. 12A along with a storage card system and protective transport packaging.

FIG. 13 is an exploded perspective view of the expandable prosthetic heart valve 140 and delivery system 142 as in FIG. 12A along with several storage cards and protective transport packaging. Specifically, the delivery system 142 along with a tubular sheath 154 mounts on a stiff first storage card 160 which, in turn, mounts to a larger second storage card 162. A pair of small protective covers 164 attach over the first storage card 160 at the proximal and distal ends of the delivery system 142. The assembly of the delivery system 142 on the cards 160, 162 is placed within a shelf box 166 having protective Styrofoam or other such protective inserts 168 therein. The shelf box 166 will desirably be constructed of paperboard with a tamper-evident carton label as an indicator of the integrity of the package. Product labeling 170 and a temperature indicator 172 for monitoring temperature during distribution and storage is attached to the shelf box 166.

Figure 14A:
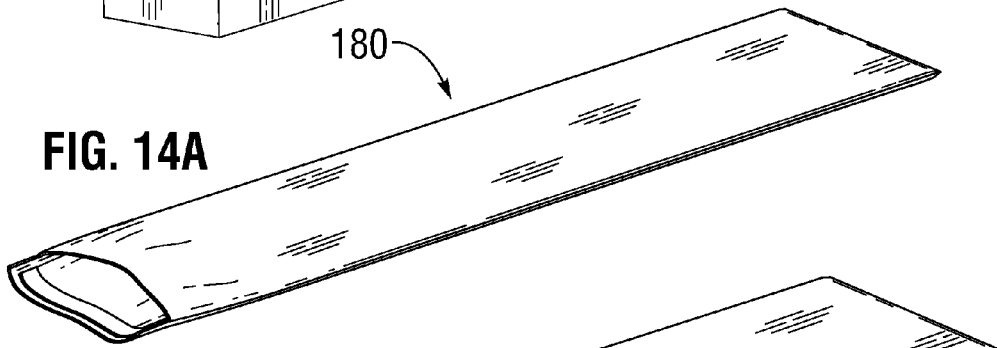
FIGS. 14A and 14B are perspective views of the primary and secondary storage containers for the assembly of FIG. 13 in the form of pouches.
Figure 14B:
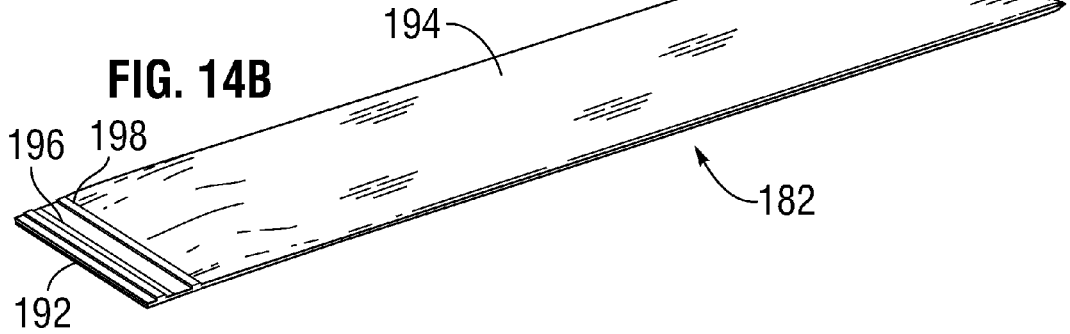

FIGS. 14A and 14B are perspective views of primary and secondary storage containers for the assembly of FIG. 13 in the form of pouches. In particular, a gas-permeable primary pouch 180 receives the shelf box 166 and then fits within a larger gas-impermeable secondary pouch 182.

In a preferred embodiment, the secondary pouch 182 includes the dual seal system mentioned above. In particular, a first gas-permeable portion 192 adjacent an open end (to the left), and a second, larger gas-impermeable portion 194 that is closed on the right end. The entire pouch 182 may be made of the gas-impermeable portion 194, except for a strip of the first portion 192 on the upper layer, or the first portion 192 may form both the upper and lower layers of the pouch adjacent the open end. A first seal 196 extends across the width of the open mouth of the pouch 182 in the area of the first gas-permeable portion 192. The second seal 198 also extends across the width of the pouch 182 but fully within the second gas-impermeable portion 194. During packaging, the primary storage tray 110 is placed within the pouch 182 and the first seal 196 closed, at which time the entire contents are gas-sterilized. After the assembly is sterile, the second seal 198 is closed to prevent any further oxygen ingress to the interior of the pouch 182.

The two seals 196, 198 enable gas sterilization of the contents of the pouch 182 prior to full sealing. More particularly, the first seal 196 may be closed at which time the package may be subject to ETO sterilization. Because the first seal 196 extends across the gas-permeable first portion 192, sterilizing gas can enter the interior of the pouch 182. After sterilization, second seal 198 is closed to prevent any further gas, in particular oxygen, from entering the interior of the pouch 182.

The storage pouch 182 provides a flexible secondary sterile barrier, and may be constructed of various materials or laminates having at least one gas-impermeable layer, with a foil/polyethylene fiber laminate being preferred. An inner layer of the foil material, such as available from Amcor, may feature a laminate of Low Density Polyethylene (LDPE) to facilitate seal under pressure and temperature. A tear notch on the pouch 182 may be provided for easy opening. With the second seal 198 closed, the foil pouch 182 provides an oxygen and moisture barrier after ETO sterilization.

FIG. 15 illustrates the expandable prosthetic heart valve 140 and delivery system 142 mounted in an exemplary primary storage container in the form of a tray 200 and a sheet-like gas-impermeable lid 202. The tray 200 features cavities for the valve 140 and delivery system 142 which retain and stabilize the components therein. As with the embodiment of FIG. 10, the lid 202 adheres to an upper rim 204 of the tray 200.

FIG. 16 is a perspective view of the prosthetic heart valve and delivery system in the tray as in FIG. 15 placed within a secondary storage container in the form of a pouch 206. Desirably, the secondary pouch 206 includes a dual seal system on its open end, as described, which provides both a gas-permeable portion and a gas-impermeable portion, depending on which seal is closed.

FIGS. 17A-17D and 18 illustrates a new hybrid prosthetic heart valve 210 and its delivery system 212. The heart valve 210 is termed a hybrid valve because it has a non-expandable portion in addition to an expandable portion. More particularly, the heart valve 210 includes a non-expandable valve portion 214 coupled to an expandable stent 216. Commissures of the valve portion 214 attach to a holder 218, much like the combination of the valve 20 and holder 40 shown in FIGS. 1-7. The expandable stent 216 facilitates a suture-less or near-suture-less implant technique by providing an anchoring force against the annulus. This type of valve is particularly suitable for the aortic annulus.

The illustrated delivery system 212 includes a handle 220 having a distal end 222 that attaches to the holder 218. The handle 220 includes a through bore that receives an elongated catheter 224 having a balloon 226 on a distal end thereof. Advancement of the catheter 224 through the handle 220 enables positioning of the balloon 226 within the expandable stent 216. More details on such a hybrid prosthetic heart valve 210 and its delivery system 212 are provided in U.S. patent application Ser. No. 12/821,628, filed Jun. 23, 2010, the disclosure of which is expressly incorporated herein by reference. Additionally, an alternative delivery system for such a hybrid prosthetic heart valve is disclosed in U.S. Provisional Patent Application Ser. No. 61/381,931 [ECV-6368PRO], filed Sep. 10, 2010, the disclosure of which is also expressly incorporated herein by reference.

FIG. 19 illustrates the hybrid prosthetic heart valve 210 and delivery system 212 mounted in an exemplary primary storage container in the form of a tray 230 and a sheet-like gas-impermeable lid 232. The tray 230 features cavities for the valve 210 and delivery system 212 which retain and stabilize the components therein. As with the earlier embodiments, the lid 232 adheres to an upper rim 234 of the tray 230.

FIG. 20 is a perspective view of the hybrid prosthetic heart valve and delivery system in the tray as in FIG. 19 placed within a secondary storage container in the form of a pouch 236. Desirably, the secondary pouch 236 includes a dual seal system on its open end, as described, which provides both a gas-permeable portion and a gas-impermeable portion, depending on which seal is closed.

FIG. 21 again illustrates the hybrid prosthetic heart valve 210 and delivery system 212 mounted in an exemplary primary storage container in the form of a tray 240 and a sheet-like gas-impermeable lid 242. The tray 240 features cavities for the valve 210 and delivery system 212 which retain and stabilize the components therein. The lid 242 adheres to an upper rim 244 of the tray 240.

Figure 21:
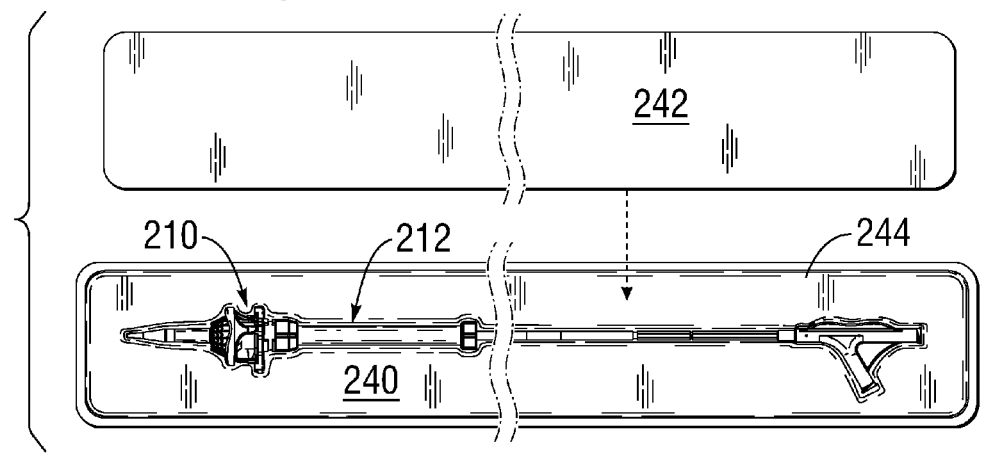
FIG. 21 is an exploded plan view of the hybrid prosthetic heart valve and delivery system as in FIG. 17B mounted in an exemplary primary storage container in the form of a tray.
Figure 22:
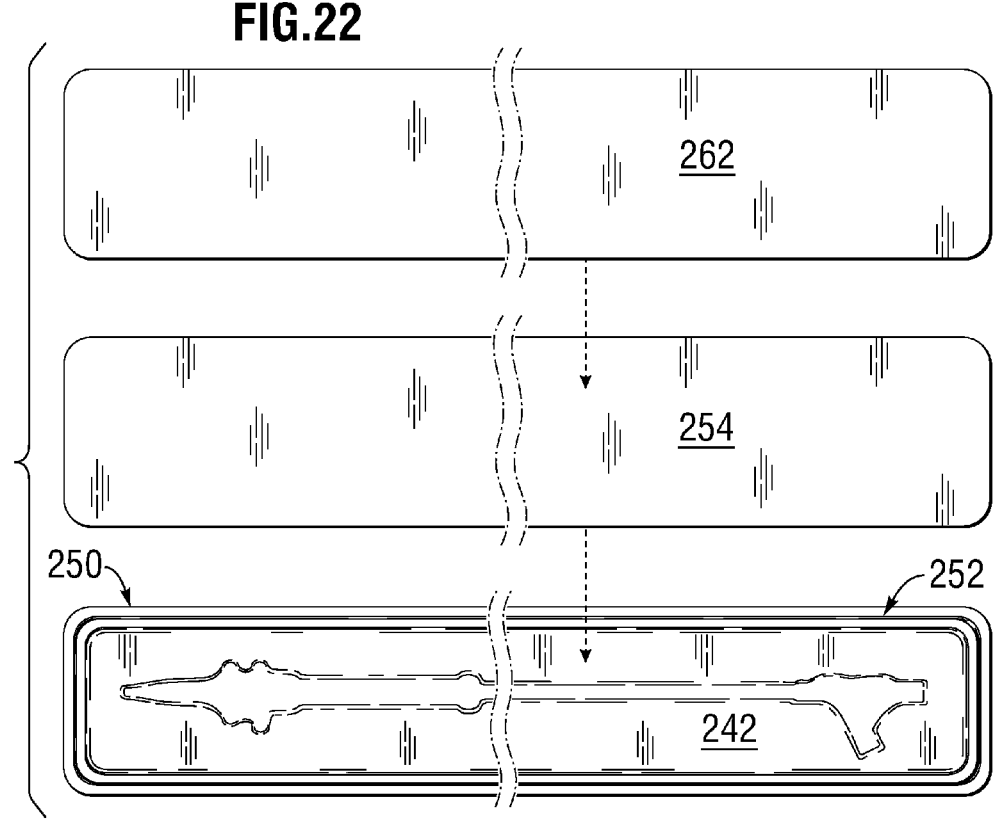
FIG. 22 is an exploded plan view of the hybrid prosthetic heart valve and delivery system in the tray as in FIG. 21 contained within a secondary storage container in the form of an outer tray.

FIG. 22 illustrates the hybrid heart valve 210 and delivery system 212 in the tray as in FIG. 21, and then placed within a secondary storage container in the form of an outer or secondary tray 250. The secondary storage tray 250 desirably mimics the shape of the primary storage tray 240 such that the latter can be easily nest within a cavity formed therein. The secondary storage tray 250 comprises an upper surface including a peripheral flange 252.

The outer storage tray 250 provides a rigid secondary sterile barrier that protects and preserves the inner sterile barrier formed by the inner storage tray 240 and its lid 242. As with the earlier primary storage trays, the outer storage tray 250 may be constructed of a gas-impermeable molded material, such as a polyethylene terephthalate copolymer (PETG). Once the sealed inner tray 240 is placed within the outer storage tray 250, a gas-permeable lid 254 seals against the flange 252 and permits sterilization gas (e.g., ETO) to reach the spaces within both trays.

Subsequently, a gas-impermeable label 262 sized to cover the secondary storage tray 250 is shown. The label 262 is applied over the sterilized tray 250, and sealed on top of the lid 254. Once pressure adhered or heat sealed against the lid, the label 262 provides a complete barrier to gas transfer. The label 262 preferably includes a layer of metal foil laminated to a layer of a gas-permeable material such as DuPont 1073B Tyvek, or more preferably is a single layer of foil. The label 262 may have information printed thereon about the contents of the packaging, such as implant type, model, manufacturer, serial number, date of packaging, etc. A layer of pressure sensitive adhesive is provided to seal on top of the previously attached lid 254.

Alternatively, the secondary storage tray 250 features a double flange (not shown) around its upper edge. And inner flange may first be sealed with a die-cut and heat seal adhesive coated gas-permeable lid (e.g., Tyvek), such as lid 254, after placement of the inner sterile barrier package, enabling subsequent ETO sterilization of the entire package, and in particular the space between the two sterile barriers. A gas-impermeable label such as the foil label 262 is then sealed to an outer flange.

The packaging solutions disclosed herein facilitate access to prosthetic heart valves and their delivery systems at the time of implantation. The process for removing the hybrid heart valve 210 and delivery system 212 of FIGS. 17-18 from its packaging will be described, though similar steps can be used to remove the other heart valves and their delivery systems. The first step is removal of the outer or secondary sterile barrier, two embodiments of which have been described (pouch or tray). This description will assume a secondary storage tray 250. One or both sealed labels over the outer tray 250 are first detached, and the inner tray 240 sealed by the sterile lid 242 (FIG. 21) removed therefrom (alternatively, the technician tears open the pouch 236 as in FIG. 20). At this stage, the inner sterile packaging may be transported to the immediate vicinity of the operation site without undue concern for the integrity of the package because of the relatively rigid inner tray 240 and sterile seal 242.

Subsequently, the technician detaches the lid 242, exposing the assembly seen in FIGS. 17-18. The delivery system 212 is then advanced over a pre-install guidewire such that the heart valve 210 is in position within the target annulus. Inflation fluid connected to a proximal luer fitting then flows to inflate the expansion balloon 226 and valve stent 216. The holder 218 is then severed from connection with the heart valve 210, and the delivery system 212 removed.

The packaging assemblies herein provide a number of distinctive advantages to manufacturers of dry prosthetic valves. Due to presence of a gas-permeable sterile barrier such as a Tyvek Header (breathable vent) the product can easily be ETO sterilized and aerated for acceptable levels of residuals. After appropriate aeration time, the outer container, or second barrier, can be sealed (e.g., foil to foil) to prevent long term oxidation of the dry tissue valve. The ETO sterilization obviates traditional oven sterilization, therefore reducing the amount of energy spent in heating the packaged product in an oven for multiple days. Similarly, elimination of autoclaving of the jars and closures before packaging will reduce the energy consumption required in the sterilization process.

As mentioned, the double sterile barrier allows for gas sterilization, such as with ETO, but also provides an oxygen barrier to the product after sterilization. Consequently, the entire assembly can be reliably stored in oxygen-free conditions for extended periods of time, even years, yet the outer sterile container can be removed at the time of use without exposing the contents of the inner sterile container to contaminants. The double layer of packaging enables sterile transfer of the inner package to the sterile operating field, and the inner package can even be temporarily stored for significant periods before the product is used. The new package design will be lighter in weight due to the choice of materials (PETG/Tyvek and air vs. Polypropylene with glutaraldehyde), which will reduce the shipping costs for single unit shipments.

Indeed, the biggest advantage over existing "wet" heart valve package designs is the elimination of storage and handling of liquid glutaraldehyde during the packaging and storage process, as well as the absence of glutaraldehyde at the time of use. This reduces hazards to the health of employees, customers, and patients, as well as the environment. Additionally, disposal of glutaraldehyde is bio-hazardous and therefore OSHA requires neutralization of the chemical before disposal or placement of appropriate controls for disposal. Due to decreased handling and critical storage requirements described herein, the packaging process is rendered less complex. The elimination of glutaraldehyde will not require an increased level of insulation from higher temperatures as the dry tissue valve already has the capability to withstand temperatures as high as 55° C. Therefore this will likely reduce the bulkiness of the design by reducing the size and insulation used for shipping the valve during summers and winters.

Current tissue valves available from Edwards Lifesciences are packaged in a 3.8 oz polypropylene jar/closure system with liquid glutaraldehyde. The presence of liquid glutaraldehyde requires the package design to maintain a state of temperature that will not overheat or freeze the tissue valve. Therefore the current package is bulky and heavier due to presence of EPS (Expanded Polystyrene) foam end caps outside the secondary package (shelf carton) which insulates from extreme temperature conditions. The polypropylene 3.8 oz jar/closure system with liquid glutaraldehyde, secondary package and foam insulation make the package design bulky and heavy resulting in increased space for storage and increased costs for shipping. The current single unit summer pack weighs approximately 0.85 lbs where as the current single unit winter pack weighs approximately 1.85 lbs. The packages disclosed herein are significantly lighter.

While the invention has been described in its preferred embodiments, it is to be understood that the words which have been used are words of description and not of limitation. Therefore, changes may be made within the appended claims without departing from the true scope of the invention.

What is claimed is:

1. A system for packaging a dry tissue heart valve and its delivery system:
   a gas-permeable primary container comprising a dry tissue heart valve and a valve delivery system, the dry tissue heart valve having an inflow end and an outflow end, the dry tissue heart valve coupled to a distal end of the valve delivery system, the dry tissue heart valve being oriented such that the outflow end is oriented proximally to the distal end of the valve delivery system and the inflow end is oriented distally from the distal end of the valve delivery system; and
   a secondary container sized to receive the primary container, the secondary container being convertible from being gas-permeable to gas-impermeable;
   wherein the valve delivery system is configured to be slidably actuated between a collapsed state and an elongated state; and
   wherein the dry tissue heart valve coupled to its valve delivery system is packaged in the primary container with the valve delivery system in the collapsed state.

2. The system of claim 1, wherein the primary container comprises a flexible pouch.

3. The system of claim 2, wherein the secondary container comprises a flexible pouch.

4. The system of claim 1, wherein the primary container comprises a relatively rigid tray.

5. The system of claim 4, wherein the secondary container comprises a relatively rigid tray.

6. The system of claim 4, wherein the secondary container comprises a flexible pouch.

7. The system of claim 1, wherein the delivery system includes a collapsible handle.

8. The system of claim 7, wherein the collapsible handle includes the telescoping sections.

9. The system of claim 1, wherein the telescoping sections include gas flow apertures open to interior lumens.

10. A method for handling a heart valve comprising: procuring a sterile package containing a prosthetic heart valve comprising an inflow end and an outflow end comprising outflow commissures removably secured to a valve holder, the valve holder including a plurality of legs shaped and dimensioned to mate with the outflow commissures, the prosthetic heart valve being stored in the sterile package without a preservative solution, the holder being coupled to a distal end of a heart valve delivery system comprising a grip section at a proximal end of the heart valve delivery system and a plurality of concentric telescoping sections, the heart valve delivery system having a collapsed state with a first length in which each section fits substantially within a cavity of an adjacent larger section and an elongated state with a second length relatively longer than the first length and the heart valve delivery system being contained in the sterile package in its collapsed state; removing the valve, the valve holder and heart valve delivery system from the sterile package; converting the heart valve delivery system from its collapsed state to its elongated state, including pulling the telescoping sections to lengthen the heart valve delivery system until adjacent telescoping sections lock together and the prosthetic heart valve is advanced distally of the grip section; and wherein all of the telescoping sections but a proximal telescoping section includes outwardly directed sealing sections on proximal ends thereof, and all of the telescoping sections but a distal telescoping section includes an inwardly-directed lip on distal ends thereof and an inwardly-directed circular feature spaced closely from distal ends thereof, wherein converting the heart valve delivery system to the elongated state locks each sealing section in a region between the inwardly-directed lip and the inwardly-directed circular feature of the adjacent telescoping section.

11. The method of claim 10, wherein the telescoping sections are generally tubular and gradually enlarge in diameter from a distal telescoping section to a proximal telescoping section, and wherein the grip section comprises undulations for receiving fingers of a user.

12. The method of claim 10, wherein the telescoping sections include interfering lips that prevent any one section from passing completely within another section and that prevent the sections from disengaging past the elongated state.

13. The method of claim 10, further including elastomeric seals provided between adjacent telescoping sections to provide frictional tightness between the telescoping sections.

14. The method of claim 10, wherein a distal telescoping section of the heart valve delivery system has a locking head projecting in a distal direction and the valve holder includes a handle coupler extending in a proximal direction and having structure sized and shaped to mate with the locking head of the heart valve delivery system so that the prosthetic heart valve extends distally from the distal telescoping section of the heart valve delivery system, and wherein the locking head is elastomeric and the structure on the handle coupler sized and shaped to mate with the locking head comprises an internal cavity into which the elastomeric locking head closely fits.

15. The method of claim 10, wherein the prosthetic heart valve is a dry tissue valve and the sterile package contains no liquid preservative.

16. The method of claim 15, wherein the sterile container includes a primary container and a secondary container, the primary container having a gas-permeable seal that provides a sterile barrier preventing passage of liquid water and providing gas flow passages therewithin around the heart valve, the sealed primary container being placed within the secondary container, the secondary container including a dual seal with a gas-permeable seal inside of a gas-impermeable seal capable of preventing oxygen or water from passing therethrough, the method further including:
   removing the gas-impermeable seal from the secondary container and subjecting the sterile container to gas-based sterilization;
   removing the gas-permeable seal from the secondary container;
   removing the gas-permeable seal from the primary container; and
   performing the step of removing the valve, holder and heart valve delivery system from the sterile package.

17. The method of claim 16, wherein the primary container is a tray having an upper surface and a cavity surrounded by an upper rim and descending downward therefrom, the tray being made of gas-impermeable material, wherein the dry tissue heart valve and its delivery system are placed in the tray cavity.

18. The method of claim 16, wherein the secondary container comprises a flexible pouch.

19. The method of claim 1, further comprising a valve holder attached to a distal end of the delivery system, wherein the outflow end of the dry tissue heart valve comprises outflow commissures and the valve holder secures the outflow commissures.

\* \* \* \* \*